(12) United States Patent
Kim et al.

(10) Patent No.: US 6,896,910 B2
(45) Date of Patent: May 24, 2005

(54) ANTI-FATIGUE AND TONIC AGENT CONTAINING WILD GINSENG

(75) Inventors: Won Kyu Kim, Bangbae Pine Villa #101, 12-11, Bangbae bon-dong, Seocho-gu, Seoul (KR); Kye Won Lee, Pyungtaek-si (KR); Sun Jung Lee, Whaseong-si (KR); Bong Jun Kim, Ohsan-si (KR); Hye Young Lee, Cheongjoo-si (KR); Chul Hong Park, Pusan-si (KR); Dong Soo Kim, Pyungtaek-si (KR); Kyeong Bum Choi, Seoul (KR); Eun Joung Yoo, Ohsan-si (KR)

(73) Assignee: Won Kyu Kim, Seoul (KR)

( * ) Notice: Subject to any disclaimer, the term of this patent is extended or adjusted under 35 U.S.C. 154(b) by 0 days.

(21) Appl. No.: 10/055,344

(22) Filed: Jan. 25, 2002

(65) Prior Publication Data

US 2003/0031732 A1 Feb. 13, 2003

(30) Foreign Application Priority Data

May 15, 2001 (KR) ........................................ 2001-26424

(51) Int. Cl.[7] .............................................. A01K 35/78
(52) U.S. Cl. ...................... 424/725; 424/728; 424/757; 424/750; 424/773
(58) Field of Search .............................. 424/195.1, 725, 424/728, 757, 750, 773

(56) References Cited

U.S. PATENT DOCUMENTS

| | | | | | |
|---|---|---|---|---|---|
| 5,567,424 A | * | 10/1996 | Hastings | ................... | 424/195.1 |
| 5,773,241 A | * | 6/1998 | Ericsson | ....................... | 431/41 |
| 6,280,776 B1 | * | 8/2001 | Sha et al. | ................... | 424/728 |
| 2001/0055624 A1 | * | 12/2001 | Sha et al. | ................... | 424/725 |
| 2002/0114873 A1 | * | 8/2002 | Lee | ........................... | 426/589 |

OTHER PUBLICATIONS

Brown, T: Tom Brown's Guide to Wild Edible and Medicinal Plants; 1985, The Berkley Publishing Group, New York, NY, p. 32.*

Castleman, M. :The Healing Herbs; 1991, Rodale Press, Emmaus, PA, pp. 193–194.*

Lust, J. : The Herb Book; 1974; Bantam Books, New York, NY, p. 207.*

* cited by examiner

*Primary Examiner*—Patricia Leith
(74) *Attorney, Agent, or Firm*—Birch, Stewart, Kolasch & Birch, LLP

(57) ABSTRACT

Disclosed is an anti-fatigue and nutritious tonic agent containing powder of wild ginseng, optionally in admixture with a herb medicine, or water extract of the powder, which has remarkably enhanced anti-fatigue, and nutrition and tonic effects as compared with agents containing cultivated ginseng.

9 Claims, 3 Drawing Sheets

NATURAL WILD GINSENG

NATURAL WILD GINSENG

CULTIVATED GINSENG

ANTI-FATIGUE AND TONIC AGENT CONTAINING WILD GINSENG

TECHNICAL FIELD

The present invention relates to an anti-fatigue and tonic agent containing wild ginseng. More specifically, the present invention relates to an anti-fatigue and nutritious tonic agent containing powder of wild ginseng, mixed powder of wild ginseng and herb medicine, or water extract of the powder, as the active ingredient, and to a process for preparing the same.

BACKGROUND ART

Wild ginseng is classified into natural wild ginseng, woods grown ginseng, and wild stimulated ginseng. Natural wild ginseng is naturally growing ginseng in deep mountains. Before the beginning of cultivation of ginseng in Korea, wild ginseng has been gathered and used. However, due to an increasing demand on wild ginseng, resources for wild ginseng have been exhausted and gathering wild ginseng in the nature has become very difficult. Therefore, such a demand could not be satisfied, and thus, cultivating ginseng was tried. From the beginning of cultivation of ginseng, cultivation technologies have been continuously developed. Further, ginseng cultivators have continued to choose individual species of ginseng having superior characteristics and quantities of roots, intentionally or customarily. Both of Korea ginseng currently cultivated and wild ginseng fall within the same species, *Panax ginseng*. However, cultivated ginseng can be remarkably distinguished from wild ginseng not only in the growth rate but also in morphologies of stem and leaf, and root. Such a distinction resulted from selection of individual species continuously carried out for a long period of time since the cultivation of ginseng was begun. Differences between wild ginseng and cultivated ginseng are as follows. FIGS. 1 and 2 show schematic appearances of wild ginseng and cultivated ginseng, respectively. As shown in the Figures, wild ginseng has slim and long rhizome (1), which is formed one a year; slim and long main root (2) having flavor, the more of which is the better; hard fine roots (3) having high tensile strength; and nodule (on fine roots) (4), which is similar to nodosity. It is gold-colored, tastes sweet and bitter and has flavor. In comparison, cultivated ginseng has short 1–2 layered rhizome (1'); short thick main root (2'); many white fine roots (3'), which are weak and thus, easily torn apart. It has bitter and sweet taste, but no flavor like wild ginseng.

Main chemical ingredients of ginseng are alkaloids, saccharides, organic acids, lipophilic ingredients, nitrogen-containing compounds, vitamins and inorganic ingredients including glycoside (saponins). The most important ingredients for pharmacological effects of ginseng are saponins, and alkaloids whose activity has not yet been clearly verified. A number of kinds of saponins are contained in ginseng, whose representative example is ginsenoside $Rb_1$. Ginsenoside $Rb_1$ has various pharmacological effects: e.g. control of central nerve system; hypnotic, analgesic, sedative and antipyretic effects; stimulation of synthesis of serum proteins; inhibition of degradation of neutral fats, or stimulation of synthesis thereof (insulin-like effect); stimulation of biosynthesis of cholesterol; stimulation of synthesis of RNA; stimulation of secretion of adrenal cortical hormone; improvement of learning memory; and inhibition of eating. *Panax ginseng* C. A. Meyer has been reported to have effects of nutrition and tonic, excitation of nerve system, stimulation of secretion of adrenal cortical hormone, promotion of sexual functions, heart tonic, decrease in blood glucose, improvement of appetite, anti-anaphylaxis, anti-diuretic, anti-stress, anti-fatigue, promotion of recovery from fatigue, reinforcement of immune functions, etc. However, such pharmacological effects are complex and various, not by a single ingredient.

In contrast, wild ginseng's pharmacological effects have not yet been identified, but is expected to have similar effects to those of cultivated ginseng.

Lycii Fructus is known to have effects of nutrition and tonic, promotion of regeneration of liver cells, improvement of liver functions, and clearance of eyes. Cnidii rhizoma has an anti-blood stagnation effect, and thus, is used for sedation, the therapy of anemia and headache. *Angelicae gigantis* Radix has effects of complementation of blood and tonic, and activation of blood, and thus, is used for therapy of woman diseases from blood circulation disorders. Therefore, a mixture of the above ingredients has a high calorie and effects as a heath supplement, which has not yet been experimentally verified. Particularly, ginseng has been extensively studied for its ingredients. However, because wild ginseng (natural wild ginseng), distinguished from cultivated ginseng, is very expensive and has limited quantities, it has not yet been sufficiently studied for its ingredients. Moreover, a composition or formulation containing wild ginseng as a principal agent has never been developed, since wild ginseng has been taken raw or in a soup boiled down. That is, a nutritious tonic agent containing wild ginseng as a principal agent has never been manufactured and marketed.

On the other hand, the physiological and biochemical mechanism by which the body feels fatigue has been already known. Some known methods for evaluating fatigue are "Forced Swimming Test", measuring swimming and rest times in animals, and "Stimulation Unit of Activity ($SUA_{33}$) Test" expressed as a dose of compound needed to extend the period of time of motion by 33%, in the time of walking on a rope. However, the above methods are not desirable experimental models because of large variations among individual animals. Therefore, it has been needed to construct a new model for measurement of an anti-fatigue effect.

DISCLOSURE OF THE INVENTION

The present inventors performed extensive studies to develop a new agent having superior anti-fatigue and nutritious tonic effects than the known agents. As a result, the inventors formulated a composition containing powder of wild ginseng, instead of cultivated ginseng, optionally in admixture with a herb medicine, or water extract of the powder. The inventors then measured its pharmacological efficacy by analysis of the contents of total saponin and ginsenoside $Rb_1$ for comparison. In addition, the inventors improved the prior measurement method of an anti-fatigue effect, and developed "4% weight-loaded swimming test" measuring the swimming time under a certain load to the body weight of an animal, whereby the anti-fatigue effect was evaluated, and so completed the present invention.

Therefore, an object of the present invention is to provide a new anti-fatigue and nutritious tonic agent containing powder of wild ginseng or mixed powder of wild ginseng and herb medicine, or water extract of the powder, and a process for preparing the same.

One aspect of the present invention provides an anti-fatigue and nutritious tonic agent composition containing powder, obtained by powdering wild ginseng alone or by further mixing the obtained powder with powder of one or more herb medicines, conventionally used in nutritious tonic agents, as the active ingredient. Another aspect of the present invention provides an agent containing water extract of the powder, obtained by extracting the above powder with water at 120 to 140° C. for some time, as the active ingredient.

The herb medicine, employable in the present invention, may be any one conventionally used in nutritious tonic agents. Examples thereof include *Lycii Fructus, Cnidii Rhizoma, Angelicae gigantis Radix*, cultivated ginseng, *Acanthopanacis Cortex, Cervi parvum Cornu, Cervi Cornu,* royal jelly, honey, *Radix Codonopsis, Astragali Radix, Atractylodis Rhizoma, Dioscoreae Radix, Glycyrrhizae Radix, Amomi Cardamomi Fructus, Zizyphi Fructus, Paeoniae Radix, Rehmanniae Radix Preparata, Polygoni multiflori Radix, Adenophorae Radix, Liriopis Tuber, Asparagi Tuber, Polygonati Rhizoma, Testudi plastrum, Morindae Radix, Epidedii Herba, Eucommiae Cortex, Cibotii Rhizoma, Cordyceps*, etc.

The present composition may further contain vitamins or its analogues, amino acids, grains or vegetables as auxiliaries.

Vitamins or analogues thereof, employable in the present invention, include vitamin A, vitamin $B_1$ or acid addition salts (e.g. nitrate) thereof, vitamin $B_2$, vitamin $B_6$, vitamin $B_{12}$ or acid addition salts thereof, vitamin C, vitamin D, vitamin E, choline, nicotinic amide, pantothenic acid or salts thereof, folic acid, taurine, biotin, inositol, lecithin, DHA powder, fructo-oligosaccharide, casein phosphopeptide, galacto-oligosaccharide, glucosamine, foremilk protein powder, skim milk, magnesium hydroxide or ionic calcium. They can be used at an amount of an ordinary range.

Amino acids, employable in the present invention, include glycine, alanine, valine, norvaline, leucine, isoleucine, phenylalanine, tyrosine, surinamine, threonine, serine, proline, hydroxyproline, tryptophane, thyroxine, methionine, cystine, cysteine, asparaginic acid, glutamic acid, lysine, arginine and histidine. They can be used at an amount of an ordinary range.

Grains or vegetables, employable in the present invention, include glutinous rice, unpolished rice, Job's-tear, barley, soy bean, pumpkin, and mung bean.

In the present invention, one or more selected from pectin, sodium CMC, sodium arginate, glycine, etc. may be used as a thickening agent. One or more selected from sucrose, aspartame, micronized saccharide, oligosaccharide, isomerized saccharide, glucose, maltose or other saccharides may be used as a sweetener. One or more selected from water, ethanol or glycerin may be added as a diluent. The present composition may contain a natural organic acid such as citric acid, as an organic acid, which plays a role as a pH adjuster (preservative) and vitamin C stabilizer. As a preservative, one or more of sodium benzoate, methyl p-oxybenzoate, ethyl p-oxybenzoate, propyl p-oxybenzoate and other conventional food preservatives may be used in the present invention. They can be used according to standards for use of food additives. As flavor, ginseng flavor, honey flavor, herb flavor, orange flavor, lemon flavor, strawberry flavor or other edible natural or artificial flavors may be added. They can be used at an amount of an ordinary range.

The present composition preferably contains wild ginseng of 5–100 parts by weight, particularly 10–80 parts by weight, herb medicines of 100 parts by weight or less, vitamins of an ordinary amount or less, amino acids of an ordinary amount or less, and grains and vegetables of 200 parts by weight or less.

The present composition can be formulated into conventional dosage forms in food engineering or pharmaceutical field, such as powder, granules, tablets, capsules, solution, suspension, solution for injection, jam, syrup, essence, or concentrated solution, by additionally including one or more engineered foods or pharmaceutically acceptable carriers. The formulations can be administered via conventional routes in pharmaceutical field, such as orally or parenterally, for example, by injection or transdermal absorption. Wild ginseng powder or water extract thereof may be administered within a range of conventional dosage of ginseng.

BEST MODE FOR CARRYING OUT THE INVENTION

Figure 1:
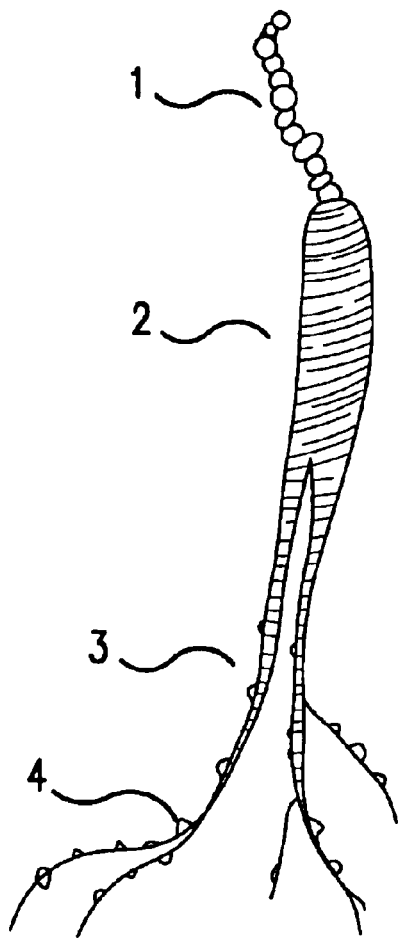
FIG. 1 shows an appearance of wild ginseng.
Figure 2:
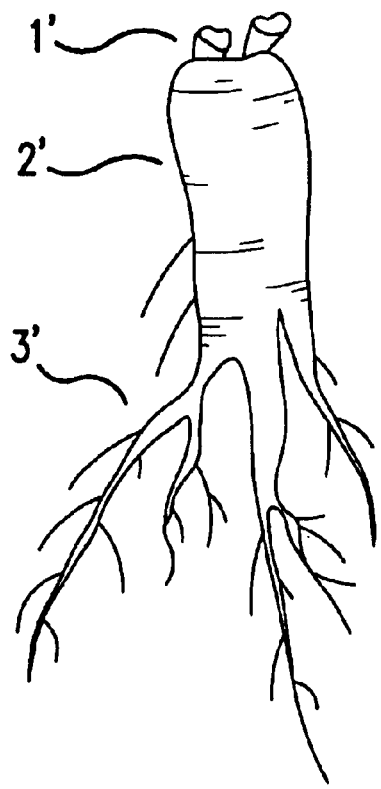
FIG. 2 shows an appearance of cultivated ginseng.

This invention will be better understood from the following examples. However, one skilled in the art will readily appreciate the specific materials and results described are merely illustrative of, and are not intended to, nor should be intended to, limit the invention as described more fully in the claims, which follows thereafter. Unless otherwise specifically stated, the term 'wild ginseng' means 'dried wild ginseng' and the term 'weight' means 'dried weight'.

EXAMPLE 1

Wild ginseng powder was prepared by powdering a dried wild ginseng of 1 g.

EXAMPLE 2

A dried wild ginseng of 1 g was powdered and extracted with purified water at 120 to 140° C. for 3 hours. The obtained extract was concentrated under reduced pressure to give about 0.2 g of wild ginseng powder extract.

EXAMPLE 3

A dried wild ginseng of 1 g was powdered and extracted with purified water at 120 to 140° C. for 3 hours. The obtained extract was concentrated under reduced pressure. Thereto was added 1 g of lactose and the mixture was dried to give about 0.2 g of extract of mixed powder of wild ginseng with lactose added.

EXAMPLE 4

| | |
|---|---:|
| Wild ginseng | 1725 mg |
| Acanthopanacis Cortex | 230 mg |
| Cnidii Rhizoma | 575 mg |
| Angelicae gigantis Radix | 575 mg |
| Lycii Fructus | 575 mg |
| Cervi Parvum Cornu | 23 mg |
| Lyophilized royal jelly | 230 mg |
| Honey | 184.179 g |
| Glucose | 345 mg |
| Micronized saccharide | 41.525 g |
| Pectin | q. s. |

Wild ginseng, Acanthopanacis Cortex, Cnidii Rhizoma, *Angelicae gigantis* Radix, Lycii Fructus and *Cervi parvum*

Cornu, in the powder state, were added to purified water at 120 to 140° C. and the mixture was extracted for 3 hours. The extract was filtered and concentrated. Thereto were added lyophilized royal jelly, honey, glucose, micronized saccharide, and pectin, and the whole mixture was stirred. The obtained mixture was cooled and coagulated to give jam.

EXAMPLE 5

| Ingredient | Amount |
|---|---|
| Wild ginseng powder | 200 mg |
| Lycii Fructus powder | 66.6 mg |
| Cnidii Rhizoma powder | 66.7 mg |
| Angelicae gigantis Radix powder | 66.7 mg |
| Cultivated ginseng powder | 2 g |
| Glutinous rice powder | 50 mg |
| Unpolished rice powder | 50 mg |
| Job's-tear powder | 50 mg |
| Barley powder | 50 mg |
| Soy bean powder | 50 mg |
| Mature pumpkin powder | 400 mg |
| Vitamin $B_1$ nitrate | 1.3 mg |
| Vitamin $B_2$ | 1.5 mg |
| Vitamin C | 55 mg |
| Vitamin $B_6$ chloride | 1.3 mg |
| Vitamin $B_{12}$ | 0.001 mg |
| Nicotinic amide | 17 mg |
| Calcium pantothenate | 3 mg |
| Folic acid | 0.25 mg |
| Vitamin $D_3$ | 3 mg |
| Taurine | 10 mg |
| Inositol | 20 mg |
| L-arginine | 50 mg |
| Biotin | 0.015 mg |
| Lecithin | 20 mg |
| DHA powder | 50 mg |
| Fructo-oligosaccharide | 30 mg |
| Casein phosphopeptide | 40 mg |
| Diet fiber | 50 mg |
| Pectin | 5 mg |
| Magnesium hydroxide | 40 mg |
| Ionic calcium | 20 mg |
| Galacto-oligosaccharide | 50 mg |
| Glucosamine | 5 mg |
| Foremilk protein powder | 10 mg |
| Skim milk | 13.4277 g |
| Aspartame | 30 mg |
| Micronized saccharide | 3 g |

The above ingredients were intimately mixed to give 20 g of granules according to a conventional method for manufacturing granules.

EXAMPLE 6

| Ingredient | Amount |
|---|---|
| Wild ginseng powder | 4.725 g |
| Lycii Fructus powder | 1.575 g |
| Angelicae gigantis Radix powder | 1.575 g |
| Cnidii Rhizoma powder | 1.575 g |

The above mixed powder was extracted with purified water at 120 to 140° C. for 3 hours. The obtained extract was concentrated under reduced pressure to give powder extract of about 1.89 g.

EXAMPLE 7

| Ingredient | Amount |
|---|---|
| Extract of Example 6 | |
| Cervi Parvum Cornu extract | 5.7 mg |
| Raw royal jelly | 10 mg |
| Honey | 5 g |
| Sucrose | 2.5 g |
| Concentrated glycerin | 1 g |
| Ethanol | 0.5 ml |
| Sodium benzoate | 285 mg |

The above ingredients were mixed, and purified water was added thereto to give a concentrated solution of a total volume of 50 ml.

EXAMPLE 8

| Ingredient | Amount |
|---|---|
| Wild ginseng herb extract | 0.3% |
| (Wild ginseng 50%, | |
| Lycii Fructus 16.66%, | |
| Angelicae gigantis Radix 16.67% | |
| and Cnidii Rhizoma 16.67%) | |
| Cervi Parvum Cornu extract | 0.1% |
| Vitamin C | 0.3% |
| Vitamin $B_1$ nitrate | 0.01% |
| Vitamin $B_2$ | 0.001% |
| Vitamin $B_6$ chloride | 0.001% |
| Nicotinic amide | 0.01% |
| Calcium pantothenate | 0.05% |
| Glycyrrhizae Radix extract powder | 0.16% |
| Lactose | 0.213% |
| L-arginine | 0.5% |
| Liquid fructose | 10% |
| Glycerin | 4% |
| Sucrose | 1% |
| Citric acid | 0.38% |
| Sodium benzoate | 0.058% |
| Xanthan gum | 0.1% |
| Stevioside (50%) | 0.03% |
| Ginseng flavor | 0.5% |
| Honey flavor | 0.2% |
| Herb flavor | 0.2% |
| Purified water | 81.887% |

Mixed powder of wild ginseng and herb medicines was added to purified water at 120 to 140° C., and then, was extracted for 3 hours. The obtained extract was filtered and the filtrate was concentrated under reduced pressure. The concentrate was dried at a low temperature to give powder extract. Liquid fructose, glycerin, sucrose, citric acid, sodium benzoate, xanthan gum and stevioside were added to purified water at 90 to 95° C., and the mixture was stirred to the complete dissolution. The above solution was cooled down to 30° C., and L-arginine, ginseng flavor, honey flavor and herb flavor were added thereto. The mixture was stirred and filtered. The filtrate was instantaneously sterilized for 20 seconds at 135° C. and filled into a vial. To the above powder extract were added Cervi parvum Cornu extract, vitamin C, vitamin $B_1$, nitrate, vitamin $B_2$, vitamin $B_6$ chloride, nicotinic amide, calcium pantothenate, Glycyrrhizae Radix extract powder and lactose, and the whole mixture was filled into the upper part of the vial. The vial was sealed to give wild ginseng essence.

EXAMPLE 9

| Per 400 mg | |
|---|---|
| Wild ginseng herb extract powder | 10.0% |
| (Wild ginseng 50%, | |
| Lycii Fructus 16.66%, | |
| Angelicae gigantis Radix 16.67% | |
| and Cnidii Rhizoma 16.67%) | |
| Cervi Parvum Cornu extract | 2.5% |
| Ginseng extract | 10.0% |
| Lecithin | 2.0% |
| Palm oil | 15.0% |
| Beeswax | 5.0% |
| Bean oil | 55.5% |

Base for Soft capsule: Gelatin 68.4%, glycerin 30.55%, ethyl vanillin 0.23%, titanium dioxide 0.34%, food coloring red No.40 0.3%, food coloring blue No. 1 0.03%, food coloring yellow No. 4 0.15%

The above ingredients were introduced into a soft capsule machine and filled into soft capsules to give soft capsules.

EXAMPLE 10

| Wild ginseng | 1000 mg |
|---|---|
| Radix Codonopsis | 500 mg |
| Astragali Radix | 500 mg |
| Atractylodis Rhizoma | 250 mg |

The above ingredients were extracted with purified water at 120 to 140° C. for 3 hours. The obtained extract was filtered and concentrated under reduced pressure. The concentrate was dried to give a dry extract of about 0.45 g.

EXAMPLE 11

| Wild ginseng | 1000 mg |
|---|---|
| Lycii Fructus | 500 mg |
| Paeoniae Radix | 500 mg |
| Polygoni Multiflori Radix | 500 mg |
| Liriopis Tuber | 500 mg |

The above ingredients were extracted with purified water at 120 to 140° C. for 3 hours. The obtained extract was filtered and concentrated under reduced pressure. The concentrate was dried to give a dry extract of about 0.6 g.

EXAMPLE 12

| Wild ginseng | 1000 mg |
|---|---|
| Cnidii Rhizoma | 500 mg |
| Angelicae gigantis Radix | 500 mg |
| Rehmanniae Radix Preparata | 200 mg |
| Adenophorae Radix | 500 mg |
| Epidedii Herba | 500 mg |

The above ingredients were extracted with purified water at 120 to 140° C. for 3 hours. The obtained extract was filtered and concentrated under reduced pressure. The concentrate was dried to give dry extract.

EXAMPLE 13

| Wild ginseng | 1000 mg |
|---|---|
| Dioscoreae Radix | 500 mg |
| Zizyphi Fructus | 500 mg |
| Eucommiae Cortex | 500 mg |
| Cibotii Rhizoma | 200 mg |

The above ingredients were extracted with purified water at 120 to 140° C. for 3 hours. The obtained extract was filtered and concentrated under reduced pressure. The concentrate was dried to give dry extract of about 0.54 g.

EXAMPLE 14

| Wild ginseng | 800 mg |
|---|---|
| Epidedii Herba | 500 mg |
| Morindae Radix | 500 mg |
| Asparagi Tuber | 500 mg |
| Polygonati Rhizoma | 500 mg |

The above ingredients were extracted with purified water at 120 to 140° C. for 3 hours. The obtained extract was filtered and concentrated under reduced pressure. The concentrate was dried to give dry extract of about 0.56 g.

EXAMPLE 15

| Wild ginseng | 1000 mg |
|---|---|
| Polygonati Rhizoma | 500 mg |
| Astragali Radix | 500 mg |
| Radix Codonopsis | 500 mg |
| Polygoni Multiflori Radix | 500 mg |
| Cervi Parvum Cornu | 500 mg |

The above ingredients were extracted with purified water at 120 to 140° C. for 3 hours. The obtained extract was filtered and concentrated under reduced pressure. The concentrate was dried to give dry extract of about 0.7 g.

EXAMPLE 16

| Wild ginseng | 1000 mg |
|---|---|
| Cnidii Rhizoma | 500 mg |
| Angelicae gigantis Radix | 500 mg |
| Cardamomi Fructus | 500 mg |
| Cordyceps | 500 mg |
| Liriopis Tuber | 500 mg |

The above ingredients were extracted with distilled water for injection at 120 to 140° C. for 3 hours. The obtained extract was filtered and concentrated under reduced pressure to a total volume of 20 ml. The concentrate was filled into a vial of 5 ml and sterilized to give an injection.

EXAMPLE 17

| | |
|---|---|
| Composition of Example 11 | 200 mg |
| Cystein | 50 mg |
| Arginine | 50 mg |
| Thiamin nitrate | 0.3 mg |
| Riboflavin | 0.001 mg |
| Lactose | 200 mg |
| Magnesium stearate | 10 mg |
| Talc | 10 mg |

The above ingredients were compressed into tablets according to a conventional method for manufacturing tablets.

EXAMPLE 18

| | |
|---|---|
| Composition of Example 12 | 200 mg |
| Cervi Parvum Cornu extract | 5.7 mg |
| Raw royal jelly | 10 mg |
| Honey | 5 g |
| Sucrose | 2.5 g |
| Concentrated glycerin | 1 g |
| Ethanol | 0.5 ml |
| Sodium benzoate | 285 mg |

The above ingredients were mixed and purified water was added thereto to a total volume of 50 ml to give a concentrated solution.

EXAMPLE 19

| | |
|---|---|
| Composition of Example 15 | 200 mg |
| Lyophilized royal jelly | 230 mg |
| Honey | 184.179 g |
| Glucose | 345 mg |
| Micronized saccharide | 41.525 g |
| Pectin | q. s. |

Lyophilized royal jelly, honey, glucose, micronized saccharide and pectin were added to the composition of Example 15. The obtained mixture was stirred, and cooled and coagulated into jam.

EXAMPLE 20

| | |
|---|---|
| Composition of Example 14 | 22.5% |
| Lecithin | 2.0% |
| Palm oil | 15.0% |
| Beeswax | 5.0% |
| Bean oil | 55.5% |

Base for soft capsule: Gelatin 68.4%, glycerin 30.55%, ethyl vanillin 0.23%, titanium dioxide 0.34%, flood coloring red No. 40 0.3%, food coloring blue No. 1 0.03%, food coloring yellow No. 4 0.15%

The above ingredients were introduced into a soft capsule machine and filled into capsules to give soft capsules.

Experiment 1:
Ingredient analysis between wild ginseng and cultivated ginseng, and evaluation of their anti-fatigue effect.

Material

A composition containing mixed powder of wild ginseng in the following Table 1 (Experimental group 1), a composition containing mixed powder of cultivated ginseng, which has cultivated ginseng, instead of wild ginseng (Experimental group 2), and a physiological saline (Control group) were administered to experimental animals, respectively.

TABLE 1

Composition of wild ginseng mixed powder

| Ingredients | Contents (mg) |
|---|---|
| Wild ginseng powder | 225 |
| Lycii Fructus powder | 74.97 |
| Cnidii Rhizoma powder | 75.97 |
| Angelicae gigantis Radix powder | 75.015 |
| Per 30 ml | 450.955 |

Experimental Animals and Breeding Condition

ICR mice of 18±5 g were bred in a breeding room of Sam Sung Pharmaceutical Ind. Co., Ltd. at a temperature of 23±2° C., relative humidity of 60±2%, and illumination of 12 hrs/day. The animals were put into a mouse cage and provided with feed and water ad libitum.

Method

1) Measurement of an Anti-Fatigue Effect

Weight-loaded forced swimming test by Toshitsugu Moriura and David L., et al. was improved as follows. Because a normal mouse can swim for 30 minutes or more, it takes a long time to observe the swimming time and is difficult to determine the finish time of swimming. Therefore, a certain weight was loaded in proportion to the body weight of a mouse, and the finish time of swimming was defined at a point of time when the two eyes sink down the surface of water for 5 seconds or more. As a result, the swimming time was shortened in a weight-dependent way as set forth in the following Table 2.

TABLE 2

| Load (weight %) | The number of mice | Swimming time (min) |
|---|---|---|
| 0 | 7 | >30 |
| 2 | 7 | 20.31 ± 5.39* |
| 3 | 7 | 8.34 ± 2.29* |
| 4 | 7 | 1.10 ± 0.85* |
| 5 | 7 | 0.5 ± 0.06* |

The values are expressed as Mean ± S.D.
*Weight-dependent compared with the Control ($p < 0.001$)

From the above Table 2, it was concluded that it was the most ideal to test an anti-fatigue efficacy under the load of 4% weight to a mouse.

Based on the above result, distilled water was filled in a transparent plastic square container of 15 cm×25 cm×20 cm with the height of 15 cm. While keeping the water temperature at 37° C., the swimming time was measured. The experimental animals had been fasted for 12 hours and then, weighed. The animals were allowed to swim while hanging a lead wire of the 4% weight to the body weight on the neck. The finish time of swimming was defined at the time when the mice settled down with the two eyes' sinking for 5 seconds. The experimental animals were divided into groups consisting of 7 animals, and administered for 1 to 7 days before experimentation. A test material was orally administered for 30 minutes before experimentation.

2) Measurement of the Content of a Total Saponin

Samples of 1–2 g were added to 100 ml of water and transferred into a separatory funnel. Thereto was added 100 ml of ether, and the aqueous layer was extracted three times with 60 ml of water-saturated butanol. The combined extract was washed with 50 ml of water. The extract was dried and put into a weighed flask, and concentrated under reduced pressure (105° C., 20 minutes). Then, it was left to cool in a desiccator and weighed. The content of a total saponin was calculated by the following formula:

The content of a total saponin=$(A-B)/S$

S: The initial weight of a sample

A: The weight of a flask containing extract concentrated under reduced pressure and dried B: The weight of a flask when decreased by 0.25% or less compared with that before drying for 1 hour.

3) Measurement of Ginsenoside $Rb_1$

Samples of 3 g were taken and introduced into 50 ml of methanol. The mixture was filtered and the filtrate of 3 ml was developed on a pre-activated sep-pak. The sep-pak was washed with 10 ml of water and 15 ml of methanol, and eluted with 10 ml of methanol. The eluted solution was used as a test material. The test material was analyzed by HPLC on $C_{18}$ reverse-phase column (Luna 10$\mu$) [Flow rate: 0.6 ml/min, Mobile phase: 20% acetonitrile, Detector: UV detector (205 nm)].

Results

1) Anti-Fatigue Effect of Cultivated and Wild Ginseng Powder

Figure 3:
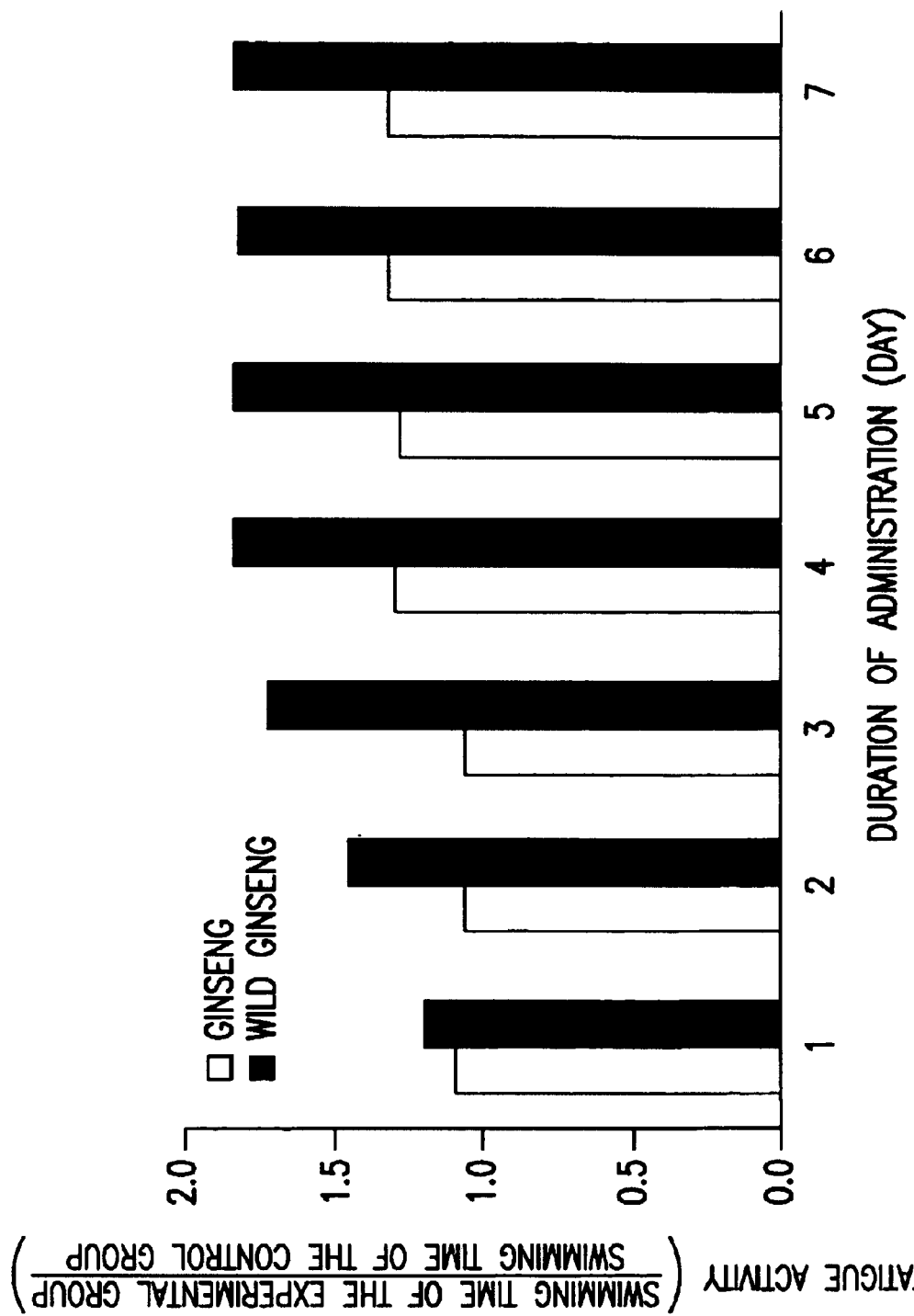
FIG. 3 is a graph comparing anti-fatigue effects of wild ginseng and cultivated ginseng.
Figure 4:
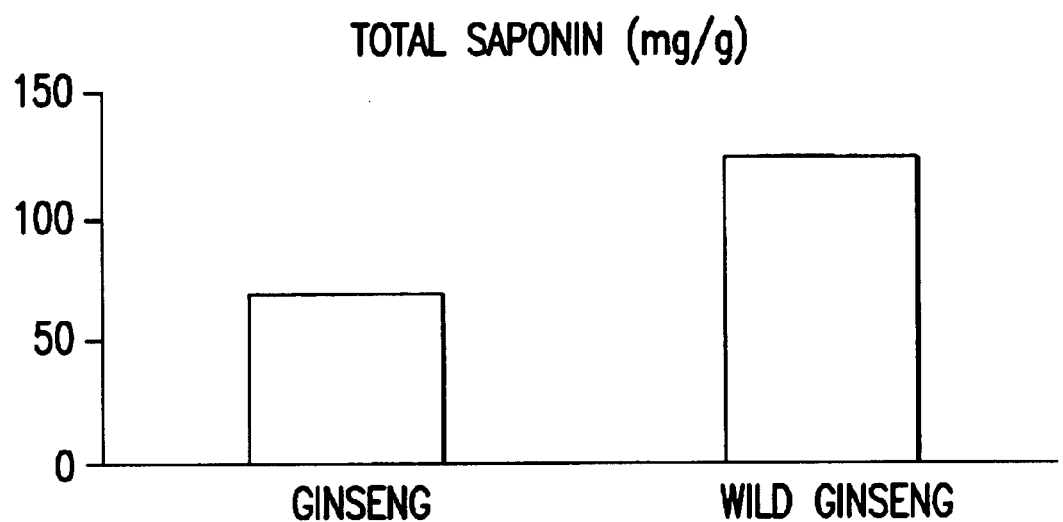
FIG. 4 is a graph comparing a total saponin of wild ginseng and cultivated ginseng.

Using the above 4% weight-loaded mice, swimming was started in 30 minutes from administration of a test material. The anti-fatigue effect of the test material was calculated by the following formula:

Anti-fatigue effect= Swimming time of the experimental group/ Swimming time of the control group The results are shown in FIG. 3. The values in FIG. 3 are Mean ±S.D. obtained from 7 mice and the symbol ** means to have a significance in p<0.01. As shown in FIG. 3, in case of administering wild ginseng powder for 4 days or more, a significantly improved anti-fatigue effect could be obtained compared with when administering cultivated ginseng powder.

Figure 5:
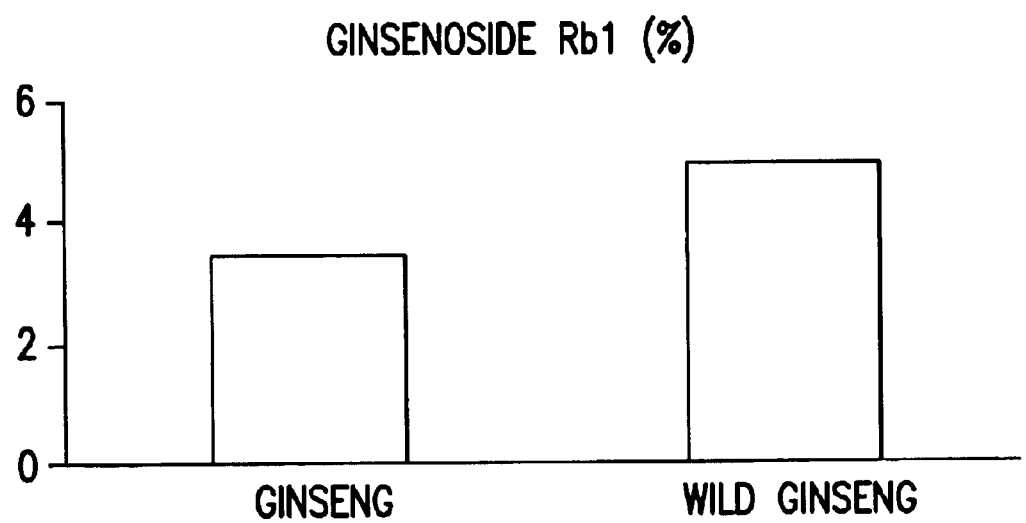
FIG. 5 is a graph comparing ginsenoside $Rb_1$ of wild ginseng and cultivated ginseng.

2) Analysis of the Content of a Total Saponin in Cultivated and Wild Ginseng Powder The measurement results of the content of ginsenoside $Rb_1$ in a sample are shown in FIG. 5. As shown in FIG. 5, the content of $Rb_1$ showed a significant difference between cultivated and wild ginseng powder.

Conclusion and Discussion

In the Experimental group administered with wild ginseng, a significant anti-fatigue effect was obtained in 4 days after administration. In the group administered with cultivated ginseng, an anti-fatigue effect could also be obtained, but was not significant. In particular, wild ginseng contains total saponin by 2 times more and a significantly higher amount of ginsenoside $Rb_1$, one of saponins, than cultivated ginseng. From such results, wild ginseng is contemplated to have much higher contents of saponins and alkaloids that are pharmacologically effective ingredients than cultivated ginseng.

INDUSTRIAL APPLICABILITY

The agent according to the present invention has much higher contents of ginseng saponins and alkaloids that are pharmacologically effective ingredients than that containing cultivated ginseng as a principal agent, and thus, exhibits excellent anti-fatigue, and nutrition and tonic effects.

What is claimed is:

1. An anti-fatigue and nutritious tonic agent containing a water extract of a mixed powder of wild ginseng, and herb medicine, wherein said herb medicine comprises, Lycii Fructus, Cnidii Rhizoma and Angelicae gigantis radix as the active ingredient.

2. The agent according to claim 1, further comprising one or more auxiliaries selected from the group consisting of vitamins and analogues thereof, amino acids, grains and vegetables.

3. The agent according to claim 2, wherein a vitamin or analogue is used and the vitamins or analogues thereof are selected from the group consisting of vitamin A, vitamin $B_1$ and acid addition salts thereof, vitamin $B_2$, vitamin $B_6$, vitamin $B_{12}$ and acid addition salts thereof, vitamin C, vitamin D, vitamin E, choline, nicotinic amide, pantothenic acid and salts thereof, folic acid.

4. The agent according to claim 2, wherein the amino acids are selected from the group consisting of glycine, alanine, valine, norvaline, leucine, isoleucine, phenylalanine, tyrosine, surinamine, threonine, serine, proline, hydroxyproline, tryptophane, thyroxine, methionine, cystine, cysteine, asparaginic acid, glutamic acid, lysine, arginine and histidine, and mixtures thereof.

5. The agent according to claim 2, wherein the grains and vegetables are selected from the group consisting of glutinous rice, unpolished rice, Job's-tear, barley, soy bean, pumpkin and mung bean, and mixtures thereof.

6. The agent according to claim 2, containing 5–100 parts by weight of wild ginseng, 100 parts by weight or less of the herb medicine, vitamins, amino acids, and 200 parts by weight or less of grains and vegetables.

7. The agent according to claim 2, further comprising one or more members selected from the group consisting of taurine, inositol, lecithin, DHA powder, fructo-oligosaccharide, casein phosphopeptide, galacto-oligosaccharide, glucosamine, foremilk protein powder, skim milk, magnesium hydroxide, and ionic calcium.

8. The agent according to claim 1, further comprising one or more carriers acceptable for foods or pharmaceuticals.

9. The agent according to claim 8, wherein said agent is formulated into powder, granules, tablets, capsules, a solution, suspension, solution for injection, jam, syrup, essence or a concentrated solution.

* * * * *